US007635792B1

(12) United States Patent
Cella et al.

(10) Patent No.: US 7,635,792 B1
(45) Date of Patent: Dec. 22, 2009

(54) 2,5-LINKED POLYFLUORENES FOR OPTOELECTRONIC DEVICES

(75) Inventors: James Anthony Cella, Clifton Park, NY (US); Joseph John Shiang, Niskayuna, NY (US); Elliott West Shanklin, Altamont, NY (US); Paul Michael Smigelski, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/250,807

(22) Filed: Oct. 14, 2008

(51) Int. Cl.
*C07C 22/00* (2006.01)
(52) U.S. Cl. ............................... 570/183; 688/1; 688/5; 544/2; 544/3; 548/100; 546/1; 546/13; 546/14; 549/4; 549/5; 549/13; 540/4
(58) Field of Classification Search .................. None
See application file for complete search history.

(56) References Cited

U.S. PATENT DOCUMENTS

| 5,708,130 | A | 1/1998 | Woo et al. |
| 5,728,801 | A | 3/1998 | Wu et al. |
| 5,777,070 | A | 7/1998 | Inbasekaran et al. |
| 5,929,194 | A | 7/1999 | Woo et al. |
| 5,948,552 | A | 9/1999 | Antoniadis et al. |
| 6,169,163 | B1 | 1/2001 | Woo et al. |
| 6,255,449 | B1 | 7/2001 | Woo et al. |
| 6,309,763 | B1 | 10/2001 | Woo et al. |
| 6,512,083 | B1 | 1/2003 | Woo et al. |
| 6,593,450 | B2 | 7/2003 | Woo et al. |
| 6,605,373 | B2 | 8/2003 | Woo et al. |
| 6,900,285 | B2 | 5/2005 | Woo et al. |

FOREIGN PATENT DOCUMENTS

| WO | 2004/060970 A1 | 7/2004 |
| WO | 2005/049546 A1 | 6/2005 |

OTHER PUBLICATIONS

Bertram et al., {Synthesis of 9-fluorenealkanamines. I: 2-(9H-Fluoren-9-yl)-2-propanamine and its aryl substituted derivatives, Archiv der Pharmazie (Weinheim, Germany) (1981), 314(4), 310-14}, Abstract.*
Courtot et al., {Fluorene series Compt. rend. (1943), 217, 453-454}, Abstract.*

* cited by examiner

*Primary Examiner*—Daniel M Sullivan
*Assistant Examiner*—Chukwuma O Nwaonicha
(74) *Attorney, Agent, or Firm*—Mary Louise Gioeni

(57) ABSTRACT

Polyfluorene polymers and copolymers having substantial amounts (10-100%) of fluorenes coupled at the 2 and 5 positions of fluorene are useful as active layers in OLED devices where triplet energies >2.10 eV are required.

23 Claims, No Drawings

2,5-LINKED POLYFLUORENES FOR OPTOELECTRONIC DEVICES

STATEMENT REGARDING FEDERALLY SPONSORED RESEARCH AND DEVELOPMENT

This invention was made with Government support under contract number DE-FC26-05NT42343 awarded by the U.S. Department of Energy. The Government may have certain rights in the invention.

CROSS REFERENCE TO RELATED APPLICATIONS

This application is related to U.S. Patent Applications, filed on even date herewith, entitled 2,5-LINKED POLYFLUORENES FOR OPTOELECTRONIC DEVICES, and identified as Ser. Nos. 12/250,826, 12/250,765 and 12/250,770, the entire contents of each of which is incorporated herein by reference.

BACKGROUND

The invention relates generally to 2,5-disubstituted fluorene monomers, oligomers and polymers derived from them and optoelectronic devices containing the oligomers and polymers.

Polyfluorene homopolymers and copolymers have emerged as preferred materials for active layers in polymer organic light emitting devices. The term "polyfluorene" commonly refers to polymers formed by linking fluorene monomer units at the 2 and 7-positions of the molecule. This linking pattern provides linear conjugation through the aryl groups, giving rise to polymers with attainable band gaps, good charge transport properties and excellent film forming properties. Moreover, functionalization of fluorene at the 2 and 7-positions is readily accomplished since these positions are the most reactive toward electrophilic reagents. Copolymerization of a 2,7-difunctional fluorene with suitable difunctional arylene monomers provides copolymers with tunable band gaps depending on the structure of the comonomers employed.

The successive accumulation of 2,7-linked fluorene segments derived from aryl coupling reactions produces conjugated arylene chains having singlet (S1) and triplet (T1) energies that vary with oligomer length up to about 7 fluorene units (Table 1). Triplet energy data of the 2,5- and 2,7-fluorene materials is partially based on "Comparison of the chain length dependence of the singlet- and triplet-excited states of oligofluorenes" in Chemical Physics Letters, vol. 411, pg. 273, Jul. 1, 2005. It can be seen that for fluorene-based material, the relative energies of the single and triplet are correlated, so that materials that exhibit higher singlet energies also exhibit higher triplet energies as well.

TABLE 1

Singlet (S1) and triplet (T1) energies for 2,7-linked fluorenes as a function of number of fluorene segments.

| # of Fluorene segments | S1 (eV) | T1 (eV) |
| --- | --- | --- |
| 1 |  | 2.85 |
| 2 | 3.35 | 2.30 |
| 3 | 3.19 | 2.25 |
| 5 | 3.05 | 2.18 |
| 7 | 3.02 | 2.16 |
| polymer | 2.97 | 2.11 |

In an OLED device, electrons and holes injected from the cathode and anode respectively combine in an emissive layer producing singlet and triplet excitons that can decay radiatively producing light or non-radiatively producing heat. For polyfluorenes and other conjugated polymers, light emission from the triplet state is a spin-forbidden process that does not compete well with non-radiative modes of decay, so triplet excitons are not very emissive. In devices based on these materials it is highly desirable to extract light from triplet excitons produced in the active layer, since there are statistically three such excitons produced for every singlet exciton. Transition metal complexes, by virtue of spin-orbit coupling, can radiatively decay with an efficiency that competes with non-radiative pathways. When these complexes are incorporated into polymeric OLED devices it is possible to achieve nearly 100% internal quantum efficiency since both singlet and triplet excitons produced in the device can emit light.

The relatively low triplet energies (Table 1) of 2,7-linked polyfluorene materials limits the transition metal complexes that can be incorporated in these devices to those that emit red or orange light from the triplet state. In order to take advantage of desirable features of polyfluorene polymers and copolymers as layers in OLED devices while expanding the color range of the phosphorescent emitters that can be used with these materials, analogues of 2,7-linked polyfluorenes having higher triplet energies are desired.

BRIEF DESCRIPTION

In one aspect, the present invention relates to compounds of formula I

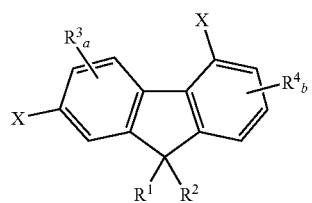

wherein $R^1$ and $R^2$ are independently at each occurrence H, $C_{1-20}$ hydrocarbyl, $C_{1-20}$ hydrocarbyl containing one or more S, N, O, P or Si atoms, $C_{4-16}$ hydrocarbyl carbonyloxy, $C_{4-16}$ aryl(trialkylsiloxy) or $R^1$ and $R^2$ taken together with an intervening carbon atom form a $C_{5-20}$ hydrocarbyl ring or a $C_{4-20}$ hydrocarbyl ring containing at least one S, N or O heteroatom;

$R^3$ and $R^4$ are independently at each occurrence $C_{1-20}$ hydrocarbyl, $C_{1-20}$ hydrocarbyloxy, $C_{1-20}$ thioether, $C_{1-20}$ hydrocarbylcarbonyloxy or cyano;

X is independently at each occurrence halo, triflate, —B(OH)$_2$, —B(OR)$_2$, —BO$_2$R, or a combination thereof;

R is alkyl or alkylene; and a and b are independently 0 or 1.

In another aspect, the present invention relates to oligomers and polymers that include at least one structural unit derived from at least one compound of formula I. In yet another aspect, the present invention relates to optoelectronic devices having an emissive layer that includes the oligomers and/or polymers.

DETAILED DESCRIPTION

The compounds of formula I have polymerizable substitutents at the 2- and 5-positions. These may be halo, and more particularly, bromo, or a borate acid or ester such as —B(OH)$_2$, —B(OR)$_2$, or —BO$_2$R, where R is alkylene, substituted or unsubstituted, or a combination of halo and borate. The monomers may be asymmetrically substituted at the 2- and 5-positions to facilitate head-to-tail-type polymerization. In the context of the present invention, head-to-tail means that during the polymerization, the each of monomers are linked between the 2-position of a first monomer and the 5-position of a second monomer. The asymmetrically substituted monomers are compounds of formula II

II

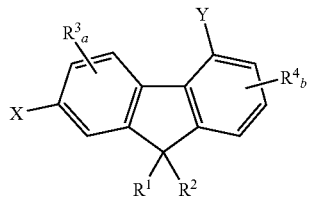

wherein one of X and Y is halo or triflate and the other one of X and Y is —B(OH)$_2$, —B(OR)$_2$, or —BO$_2$R. In some embodiments, X is halo and Y is —B(OH)$_2$, —B(OR)$_2$, or —BO$_2$R; in others, X is —B(OH)$_2$, —B(OR)$_2$, or —BO$_2$R and Y is halo. In particular, one of X and Y is bromo and the other one of X and Y is —BO$_2$R.

The compounds of formula I and formula II also mono- or disubstituted at the 9-/9,9-position. These substitutents, R$^1$ and R$^2$ are the same or different and may be alkyl, substituted alkyl, aryl, substituted aryl, heteroaryl, or substituted heteroaryl. In particular, R$^1$ and R$^2$ may be alkoxyphenyl, or alkyl.

The 2,5,9,9-substituted fluorene monomers may be additionally substituted at the 1-, 3-, 4-, 6-, 7- or 8- positions, or may be unsubstituted at these positions. In the latter case, R$^3$ and R$^4$ are H.

In particular embodiments, the compound of formula I is of formula

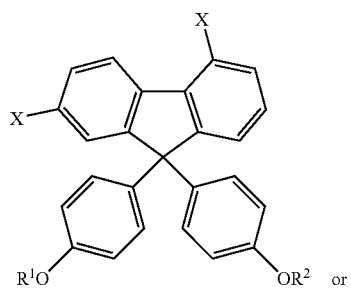 or

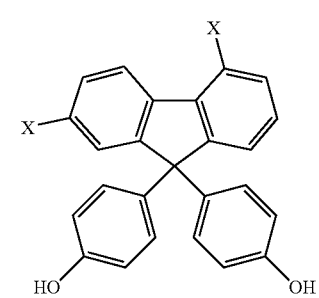

and the compound of formula II is

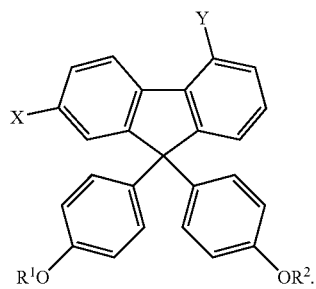

Examples of the compounds of formula I and II include

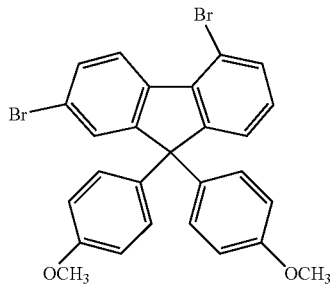

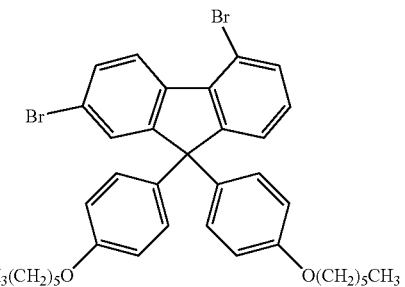

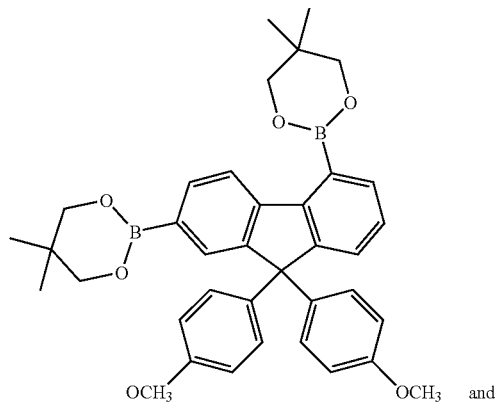 and

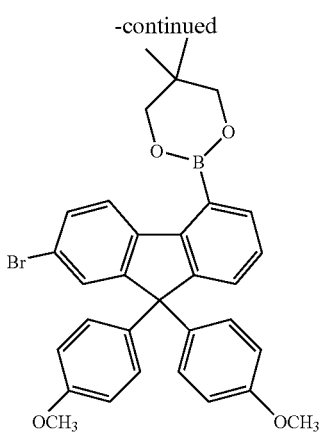

The compounds of formula I and II may be prepared by brominating fluorene or fluorenone derivatives using N-bromosuccinimide in an acidic medium at elevated temperature (40-60° C.). Direct bromination yields a substantial quantity of 2,5-dibromofluorene (15-25%). This isomer or products derived from it can be separated from the 2,7-isomer and converted to suitable monomers for polymerization, particularly the 9- and 9,9-substituted compounds. Alternatively, a mixture containing 2,5- and 2,7-dibrominated fluorene derivatives can be utilized directly to prepare copolymers. Alternatively, the 2,5-dibromosubstituted derivatives may be obtained by a rational synthetic route other than direct bromination of a fluorene derivative.

Polymers and oligomers of the present invention may be prepared by methods known in the art for making polyfluorenes, including Suzuki coupling of the appropriate dihalide and diboronate/diboronic acid and Yamamoto coupling. For example, U.S. Pat. No. 5,708,130, U.S. Pat. No. 5,777,070, U.S. Pat. No. 6,169,163, U.S. Pat. No. 6,255,449, U.S. Pat. No. 6,512,083, U.S. Pat. No. 6,593,450, and U.S. Pat. No. 6,900,285, to Dow Global Technologies, the entire contents of which are incorporated by reference, describe syntheses of polymers containing fluorene subunits.

Polymers and oligomers according to the present invention include at least one structural unit derived from at least one compound of formula I and/or II. In the context of the present invention, oligomers are distinguished from polymers by their lower molecular weight, being composed of fewer than about 20 monomer units, including compounds of formula I and II and suitable comonomers and end units, particularly fewer than about seven monomer units, and more particularly fewer than about three monomer units. In one embodiment, oligomers of the present invention are trimers; a trimer is an oligomer composed of three units, that is, two end units and a central unit. In some embodiments, the compounds of formula I and formula II are assembled in a head-to-tail configuration to form the polymers and oligomers of the present invention.

The polymers and oligomers of the present invention may additionally include compounds of formula II, that is, any of the known 2,7-substituted fluorene monomers

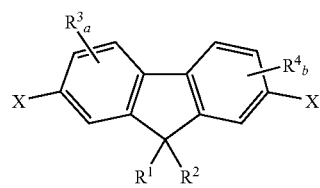

III wherein $R^1$, $R^2$, $R^3$, $R^4$, and X are defined as for the compounds of formula I and II. However, substantial (10-100%) amounts of 2,5-monomer units incorporated into polyfluorene materials may form non-fully conjugated polymers and oligomers, leading to singlet and the triplet energies of the resulting oligomers and polymers that are significantly higher than materials derived solely or predominantly from 2,7-monomer units. Accordingly, in many embodiments, the polymers and oligomers of the present invention include greater than about 50% by weight of structural units derived from the compounds of formula I and II, and particularly greater than about 90% by weight of said structural units.

Copolymerization of the compounds of formula I and II with the 2,7-disubstituted fluorene compounds of formula III and/or other monomers suitable for aryl-aryl coupling may similarly lead to copolymers having higher S1 and T1 energies than the corresponding polymers made from 2,7-disubstituted fluorene monomers. Accordingly, the polymers and oligomers of the present invention may additionally include structural units derived from conjugated compounds, including arylene monomers, particularly aryl compounds, heteroaryl compounds or triarylamines. Suitable arylmines are described in U.S. Pat. No. 5,728,801, U.S. Pat. No. 5,929,194, U.S. Pat. No. 5,948,552, U.S. Pat. No. 6,309,763, U.S. Pat. No. 6,605,373, U.S. Pat. No. 6,900,285, WO 2004/060970, WO 2005/049546 and WO 2005/052027, to Dow Global Technologies, the entire contents of which are incorporated by reference. Examples of other suitable arylene monomers include 1,4-phenylene or substituted phenylene, 1,3-phenylene or substituted phenylene, 2,6-naphthylene, 9,10 anthrylene, and compounds of formula

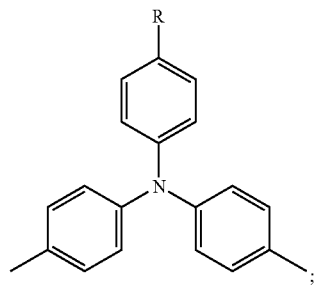

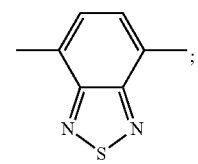

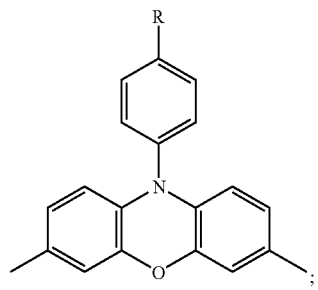

-continued
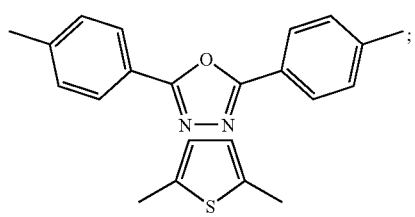
Oligomers according to the present invention may additionally include end units of formula
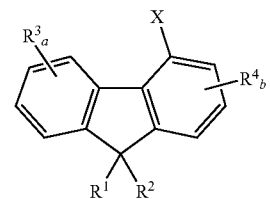
wherein $R^1$, $R^2$, $R^3$, $R^4$, and X are defined as for the compounds of formula I and II. Examples of oligomers of the present invention include
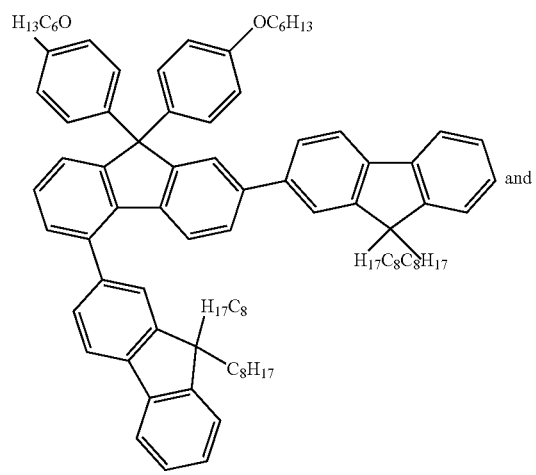
and
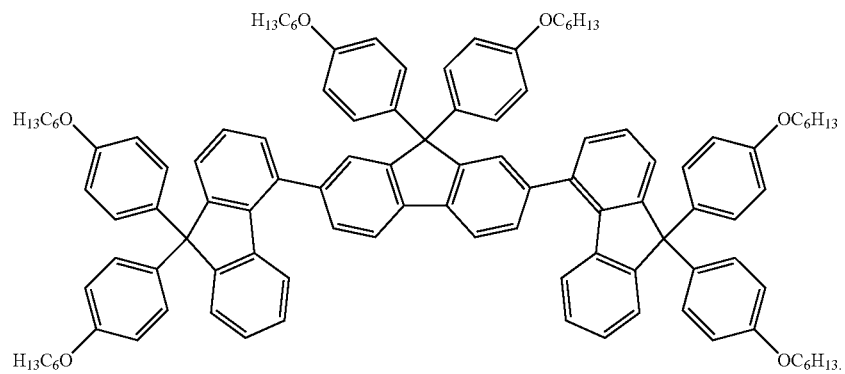

An optoelectronic device, e.g., an OLED, typically includes in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole blocking layer to prevent holes migrating toward the cathode. Additional components which may be present in an organic light-emitting device include hole transporting layers, hole transporting emission (emitting) layers and electron transporting emission (emitting) layers.

OLED devices may be fluorescent comprising a singlet emitter, or phosphorescent comprising at least one triplet emitter or a combination of at least one singlet emitter and at least one triplet emitter. The devices may contain one or more, any or a combination of blue, yellow, orange, red phosphorescent dyes, including, but not limited to, complexes of transition metals such as Ir, Os and Pt. Suitable electrophosphorescent and electrofluorescent metal complexes include those supplied by American Dye Source, Inc., Quebec, Canada may be used.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e., holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode include, but are not limited to, materials having a bulk resistivity of less than about 1000 ohms per square, as measured by a four-point probe technique. Indium tin oxide (ITO) is frequently used as the anode because it is substantially transparent to light transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to, metals and metal oxides such as ITO which can inject negative charge carriers (electrons) into the inner layer(s) of the OLED. Metals suitable for use as the cathode include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a metal, such as aluminum or silver. In particular, the cathode may be composed of a single metal, and especially of aluminum metal.

Materials suitable for use in electron transport layers include, but are not limited to, poly(9,9-mono- or disubstituted fluorene), tris(8-hydroxyquinolato) aluminum (Alq3), 2,9 dimethyl-4,7-diphenyl-1,1-phenanthroline, 4,7-diphenyl-1,10-phenanthroline, 2(4 biphenylyl)-5-(4-t-butylphenyl)-1,3,4-oxadiazole, 3-(4-biphenylyl)-4-phenyl-5 (4t butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include, but are not limited to, 1,1-bis((di-4-tolylamino)phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methyl-phenyl)-N,N,N',N'-2,5-phenylenediamine, phenyl-4-N,N-diphenylaminostyrene, p(diethylamino) benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9 yl)cyclobutane, N,N,N', N'-tetrakis-(4-methylphenyl)-(1,1'-biphenyl)-4,4'-diamine, copper phthalocyanine, polyvinylcarbazole, (phenylmethyl) polysilane; poly(3,4 ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use in the light emitting layer include, but are not limited to, electroluminescent polymers such as polyfluorenes, preferably poly(9,9-dioctyl fluorene) and copolymers thereof, such as poly(9,9'-dioctylfluorene-co-bis-N,N'-(4-butylphenyl)diphenylamine) (F8-TFB); poly (vinylcarbazole) and polyphenylene-vinylene and their derivatives. In addition, the light emitting layer may include a blue, yellow, orange, green or red phosphorescent dye or metal complex, or a combination thereof. Materials suitable for use as the phosphorescent dye include, but are not limited to, tris(1-phenylisoquinoline) iridium (III) (red dye), tris(2-phenylpyridine) iridium (green dye) and Iridium (III) bis(2-(4,6-difluorephenyl)-pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076RE, ADS067RE, and ADS077RE.

Oligomers and polymers according to the present invention may be used in hole transport, electron transport and emissive layers. For example, 50/50 copolymers formed by the reaction of a 2-5-bis-ethylenedioxaboryl-9,9-bis-(4-methoxyphenyl)-fluorene and a dibromotriarylamine are suitable for use in a hole transporting layer. Alternately, a copolymer formed by the reaction of a predominant fraction of the compounds of formula I and II with a smaller fraction of an emissive triarylamine are suitable for use in an emissive layer. Alternatively, an emissive polymer may be formed via reaction of the compounds of formula I and II, with monomers containing an emissive unit such as an electrofluorescent and electrophosphorescent metal complex attached via the 9-position of the fluorene. Examples of suitable polymerizable metal complexes are described in WO 2003/001616, to Showa Denko, WO 20050016945, to Dow Global Technologies, and WO 2008/014037, to General Electric Company, the entire contents of which are incorporated by reference. In addition, 2,5-fluorene homopolymers are suitable as both an electron transport layer and as a deep blue emissive layer. For example, the 2,5 fluorene homopolymer can be combined with a luminescent dye to form a blend material that is suitable for use as an emissive layer. The luminescent dye may be either fluorescent (emitting from a predominantly singlet state) or phosphorescent (emitting from a state that is not predominantly singlet). Furthermore, the oligomers and polymers of the present invention may also be used as a host for materials that have a specific hole-transporting, electron transporting or emissive function, for example by blending with the hole and electron transporting materials listed above in order to obtain some desired charge transport capability.

DEFINITIONS

In the context of the present invention, hydrocarbyl means any organic moiety containing only hydrogen and carbon unless specified otherwise, and may include aromatic, aliphatic, cycloaliphatic and moieties containing two or more aliphatic, cycloaliphatic and aromatic moieties, including, but not limited to, alkyl, alkylaryl, aryl, arylalkyl, and substituted analogs thereof. Hydrocarbyl containing one or more S, N, O, P or Si atoms includes, but is not limited to, alkoxy, acyl, heteroaryl, heteroaryl-alkyl, oxaalkyl, haloalkyl, and silyl, and substituted analogs thereof.

Alkyl is intended to include linear, branched, or cyclic hydrocarbon structures and combinations thereof, including lower alkyl and higher alkyl. Preferred alkyl groups are those of C20 or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, alkenyl, substituted alkenyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

Oxaalkyl refers to an alkyl residue in which one or more carbons have been replaced by oxygen. It is attached to the parent structure through an alkyl residue. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Silyl means an alkyl residue in which one to three of the carbons is replaced by tetravalent silicon and which is attached to the parent structure through a silicon atom. Siloxy is an alkoxy residue in which both of the carbons are replaced by tetravalent silicon that is endcapped with an alkyl residue, aryl residue or a cycloalkyl residue, and which is attached to the parent structure through an oxygen atom.

EXAMPLES

General

Preparation of poly-9,9-bis-(4-hexyloxy)phenyl-2,7-diyl-alt-9,9-bis-(4-hexyl-oxy)phenyl-2,5-diyl 2 from 2,5-dibromo-9,9-bis-(4-hexyloxyphenyl)fluorene 1 is depicted in Scheme 1. 2,5-Dibromo-9,9-bis-(4-hydroxyphenyl)fluorene was isolated from an ~80/20 mixture of the 2,7-dibromo and 2,5-dibromo isomers respectively. The isomeric mixture was obtained by reaction of a mixture of 2,7-dibromo and 2,5-dibromofluorenones with excess phenol in methanesulfonic acid using a polymer bound mercaptan as a promoter. The dibromofluorenone isomer mixture was obtained by bromination of fluorenone with N-bromosuccinimide in an acetic acid/methanesulfonic acid mixture at ~50° C. Isolation of the pure bis-phenol was accomplished by selective extractions followed by repeated chromatography.

Scheme 1. Preparation of Poly-9, 9-bis-(4-hexyloxy)phenyl-2, 7-diyl-alt-9, 9-bis-(4-hexyloxy)phenyl-2, 5-diyl

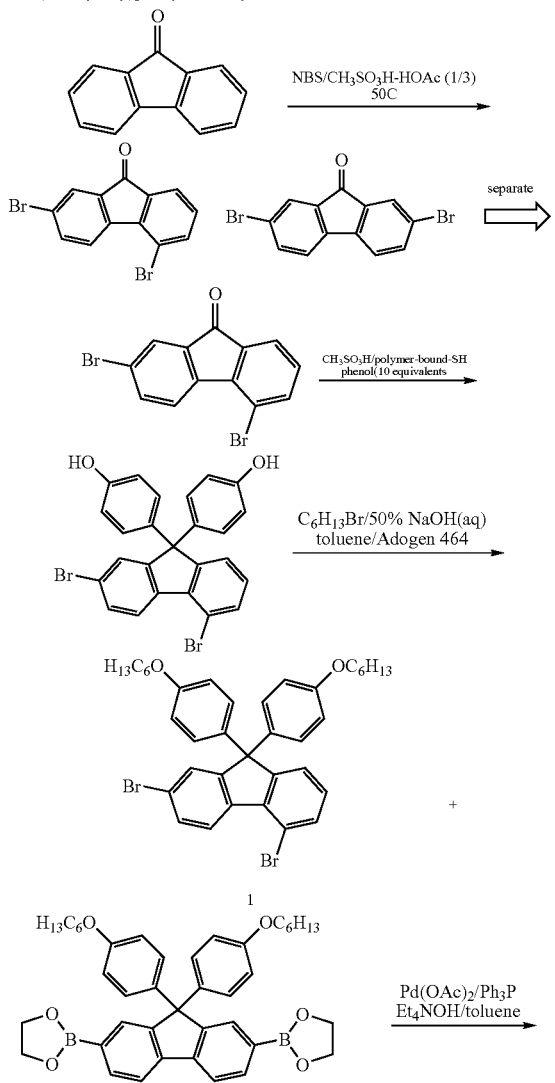

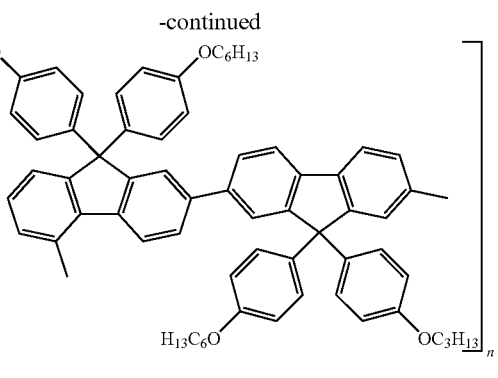

2

Example 1

Preparation of 2,5-dibromo-bis-(4-hexyloxyphenyl)fluorene, 1

A magnetically stirred mixture of 2,5-dibromo-9,9-bis-(4-hydroxyphenyl) fluorene, 2.54 g (5.0 mmol) and n-hexylbromide, 2.06 g (12.5 mmol) in toluene (10 ml) plus 50% (aq) NaOH, 1.0 ml (~5 mmol) and Adogen 464 (~100 mg) was heated at reflux for about 16 hrs. The cooled mixture was diluted with toluene (15 ml) and water (20 ml) then transferred to a separatory funnel and the aqueous phase was discarded. The organic phase was washed with water (3×25 ml) and brine (1×25 ml) then passed through a cone of Drierite. Evaporation of solvent afforded 3.4 g of a colorless oil that was chromatographed on silica gel (120 g) eluted with a hexane-ethylacetate gradient (0-10% EtOAc). The product was isolated as a colorless, tacky gum. The material was crystallized from ethanol at −20° C., but the crystals melted below room temperature.

Example 2

Preparation of poly-9,9-bis-(4-hexyloxyphenyl)fluorene-2,7-diyl-alt-9,9-bis-(4-hexyloxyphenyl)fluorene-2,5-diyl, 2

A solution of 1, 279 mg (0.413 mmol), 2,7-bis-ethylenedioxaboryl-9,9-bis-(4-hexyloxyphenyl)fluorene, 272 mg (0.414 mmol) and 2-(2,6-dimethoxyphenyl)phenyl-dicyclohexylphosphine, 17.8 mg (0.043 mmol) in toluene (25 ml) was degassed with Argon for 10 minutes and palladium acetate, 2.8 mg (0.0124 mmol) was added. In a separate flask, a 10% solution of tetraethylammonium hydroxide, 3.04 g (2.07 mmol) was degassed for 15 minutes then added to the toluene solution. The flask was immersed in an oil bath at 70° C. and was stirred under a positive $N_2$ pressure for 20 hrs. The cooled mixture was diluted with toluene and water then filtered through Celite. The aqueous phase was discarded and the organic phase was washed with water (3×50 ml) and brine (1×50 ml) then passed through a cone layered with Celite, amine-functional silica gel and Drierite. The filtrate was concentrated under vacuum to a volume of approximately 5 ml and the polymer was isolated by precipitation into methanol (~75 ml). The number average molecular weight of 2 was ~13K (relative to polystyrene standards).

Example 3

Preparation of poly-9,9-bis-(4-hexyloxyphenyl)fluorene-2,7-diyl, 3

In a similar fashion to the procedure described for the preparation of polymer 2, polymer 3 was obtained from the Pd (0) catalyzed coupling of 2,7-bis-ethylene-dioxaboryl-9,9-bis-(4-hexyloxyphenyl)fluorene with 2,7-dibromo-bis-(4-hexyloxy-phenyl)fluorene. The number average molecular weight of 3 was ~182K (relative to polystyrene standards).

Example 4

Preparation of 9,9-bis-(4-hexyloxyphenyl)2,7-bis-(9,9-dioctylfluorene-2-yl)fluorene, 4

A solution of 1, 100 mg (0.153 mmol), 2-(2,2-dimethyl)propylenedioxyboryl-9,9-dioctylfluorene, 161 mg (0.321 mmol) and 2-(2,6-dimethoxyphenyl)phenyldicyclo-hexylphosphine, 10.0 mg (0.025 mmol) in toluene (5 ml) was degassed with Argon for 10 minutes and palladium acetate, 1.5 mg (0.007 mmol) was added. In a separate flask, a 10% solution of tetraethylammonium hydroxide, 1.2 g (0.822 mmol) was degassed for 15 minutes then added to the toluene solution. The flask was immersed in an oil bath at 70° C. and was stirred under a positive $N_2$ pressure for 20 hrs. The cooled mixture was diluted with toluene and water then filtered through Celite. The aqueous phase was discarded and the organic phase was washed with water (3×50 ml) and brine (1×50 ml) then passed through a cone layered with Celite, amine-functional silica gel and Drierite. The filtrate was concentrated to dryness under vacuum affording a residue that was chromatographed on silica gel (12 g-0-10% EtOAc/hexane) to afford 150 mg (76%) of 4 as a colorless oil.

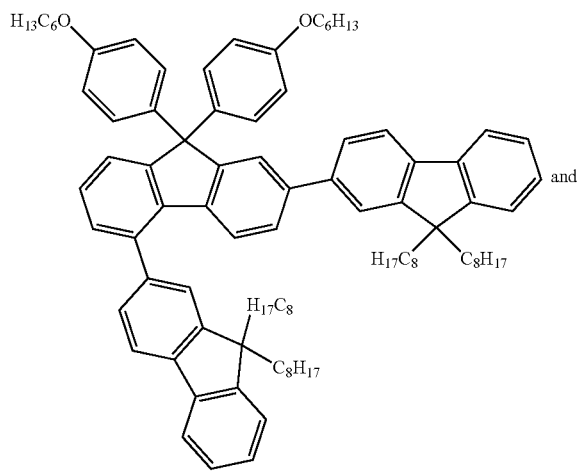

4
S1 = 3.34 eV

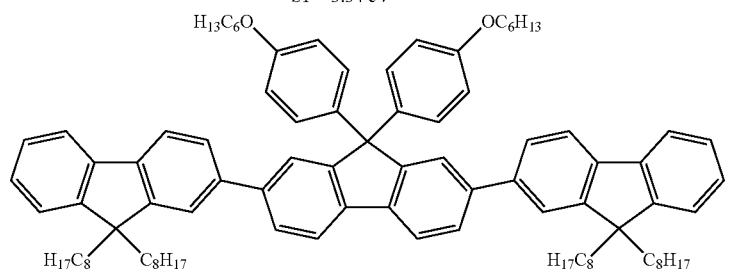

5
S1 = 3.14 eV

Example 5

Preparation of Fluorene Trimer 5

In a similar fashion, fluorene trimer 5 was prepared by condensing 2-(2,2-dimethyl)propylenedioxyboryl-9,9-dioctylfluorene with 2,7-dibromo-9,9-bis-(4-hexyloxyphenyl)fluorene. Singlet (S1) and triplet (T1) energies for polymer 2 and the corresponding 2,7-linked polyfluorene 3 are presented in Table 2. Replacement of 50% of the 2,7-linked fluorenes with 2,5-linked fluorenes led to a 0.1-0.2 eV increase in triplet energies for the all fluorene polymers.

TABLE 2

| Polymer | S1 (eV) | T1 (eV) |
|---|---|---|
| 2 | 3.14 | 2.2-2.3 |
| 3 | 2.99 | 2.14 |
| 4 | 3.34 | |
| 5 | 3.14 | |

Singlet (S1) and triplet (T1) Energies

Example 6

Preparation of 9,9-bis-(4-methoxyphenyl)fluorene-2, 5-bis-neopentylglycol boronate

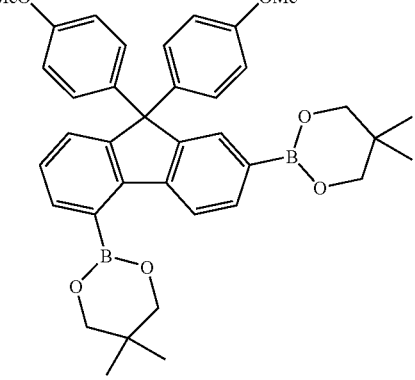

A dry, 250 ml flask equipped with a magnetic stir bar, serum stopper and a nitrogen inlet was charged with a solution of 9,9-bis-(4-methoxyphenyl)-2,5-dibromofluorene, 2.841 g (5.30 mmol) in anhydrous tetrahydrofuran (100 ml). The flask and contents were chilled to −78° C. and a solution of butyllithium in hexane (2.06M, 6.5 ml, 13.25 mmol) was added over 2-3 minutes. The light yellow solution was stirred at −78° C. for 5.5 hrs then triethylborate, 3.2 ml (18.55 mmol) was added. The mixture was allowed to warm to room temperature and was stirred overnight then quenched by addition of saturated ammonium chloride (25 ml) and 0.1 N HCl (5 ml). This mixture was transferred to a separatory funnel and the aqueous phase was extracted with ether (50 ml). The combined organic phases were washed with water (1×100 ml) and brine (1×100 ml) then filtered through a cone of anhydrous $CaSO_4$. Evaporation of solvents afforded 2.82 g of a white solid. The solid was refluxed with a mixture of chloroform (50 ml) and neopentyl glycol (1.20 g, 11.5 mmol). After one hour the cooled mixture was transferred to a separatory funnel and the organic phase was washed with brine then concentrated to afford about 4.5 g of a solid mass that was chromatographed on 120 g of silica gel eluted with 5-60% ethyl acetate in hexane. The product was isolated after chromatography on silica gel as a colorless foam, 2.36 g (74%) that was recrystallized from ether/hexane to afford colorless crystals. $^1$H NMR ($CDCl_3$) δ 8.30 (d, 1, fluorenyl-4-H), 7.80 (m, 1, fluorenyl-H), 7.75 (s, 1, fluorenyl-H) δ, 7.69 (m, 1, fluorenyl-H), 7.40 (m, 1, fluorenyl-H), 7.28 (t, 1, fluorenyl-7H), 7.12 and 6.79 (doublet of doublets (9-aryl-H), 3.94 (s, 4, borate-$CH_2$'s), 3.77 (s, 10, Ar$OCH_3$ and borate $CH_2$'s), 1.17 (s, 6, geminal $CH_3$) and 1.04 ppm (s, 6, geminal $CH_3$).

Example 7

Preparation of poly-9,9-bis-(4-methoxyphenyl)-2,5-fluorenyl-alt-N-4-butylphenyl-4,4'-diphenylamine-diyl

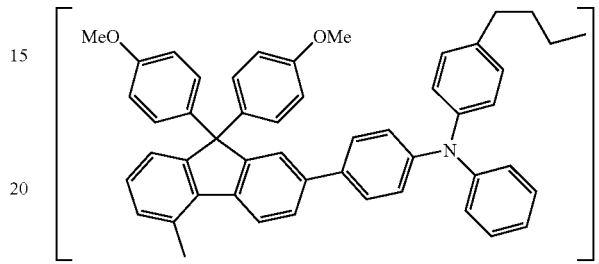

A solution of 9,9-bis-(4-methoxyphenyl)fluorene-2,5-bis-neopentylglycol boronate, 327 mg (0.543 mmol), N-4-butylphenyl-N,N-bis-4-bromophenyl-triphenylamine, 249 mg (0.543 mmol) and dicyclohexyl-2-(2,6-dimethoxyphenyl)-phenylphosphine, 16 mg (0.0385 mmol) in toluene, 12 mL was degassed with Argon for 15 minutes then palladium acetate, 2.4 mg (0.011 mmol) was added. A degassed 10% solution of tetraethylammonium hydroxide, 3.8 g was added and the mixture was immersed in a 70° C. oil bath and stirred at that temperature under nitrogen for 19 hours. The cooled mixture was diluted with water (10 ml) and toluene (20 ml) then filtered through Celite. The filtrate was transferred to a separatory funnel, the aqueous phase was discarded and the organic phase was washed with water (3×25 ml) and Brine (2×25 ml) then passed through a cone of anhydrous $CaSO_4$. The filtrate was stirred with 250 mg of amine-functional silica gel overnight then filtered. The filtrate was concentrated to a volume of about 10 ml. The concentrate was stirred vigorously while methanol, 75 ml was added in portions. The precipitate was collected by filtration and dried in a vacuum oven at 40° C. overnight. The yield was 362 mg (98%). $^1$H NMR ($CDCl_3$) δ 7.75-6.75 (m, 26, ArH), 3.80 (m, 6, arO$CH_3$), 2.65 (m, 2, N$CH_2$R), 1.60 (m, 2, N$CH_2$C$\underline{H}_2CH_2CH_3$), 1.45 (m, 2, N$CH_2CH_2C\underline{H}_2CH_3$) and 1.0 ppm (m, 3, N$CH_2CH_2CH_2C\underline{H}_3$). UV spectrum ($CH_2Cl_2$) λ max=359 nm; ε=30,563)

Example 8A

Preparation of 9,9-dioctyl-2-(9,9-bis-4-(2-morpholinoethoxyphenyl)-2,7-diyl)-9,9-dioctylfluoren-2-yl terfluorene

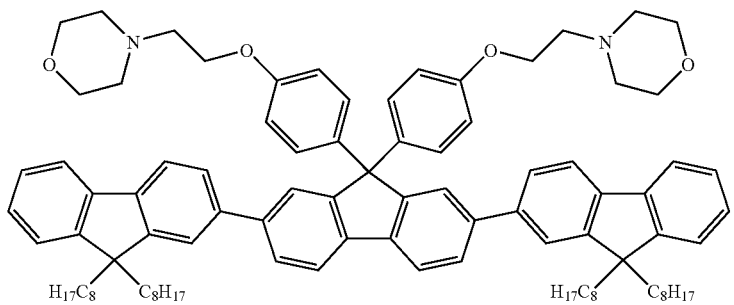

Materials: 9,9-bis-4-(2-morpholinoethoxy)phenyl-2,7-dibromofluorene was prepared by alkylation of 9,9-bis-4-hydroxyphenyl-2,7-dibromofluorene with 2-chloroethyl morpholine hydrochloride with 50% NaOH/toluene in the presence of Adogen 464 as a phase transfer catalyst; 9,9-dioctyl-2-neopentylglycol boronate was prepared by lithiation of 9,9-dioctylfluorene (BuLi, Et$_2$O/−78° C.) followed by borylation (triethoxy borate), hydrolysis and re-esterification with neopenyl glycol.

Preparation of trimer: A solution of 9,9-bis-4-(2-morpholinoethoxy)phenyl-2,7-dibromofluorene, 1.101 g (1.5 mmol), 9,9-dioctyl-2-neopentylglycol boronate, 1.544 g (3.075 mmol) and dicyclohexyl-2-(2,6-dimethoxyphenyl)phenylphosphine, 0.054 g (0.131 mmol) in toluene (30 ml) was degassed for 15 minutes then Pd(OAc)$_2$, 0.084 g (0.0375 mmol) and 10% aqueous tetraethylammonium hydroxide, 11 g that had been separately degassed was added. The stirred mixture was immersed in a 70° C. oil bath and stirred under nitrogen for 18 hrs. The cooled mixture was filtered and transferred to a separatory funnel. The aqueous phase was discarded and the organic phase was washed with water (3×50 ml) and brine (1×50 ml) then passed through a cone of anhydrous CaSO$_4$. Removal of solvent afforded a white foam that was purified by chromatography on 80 g of alumina (neutral)-yield, 1.23 g (60%). $^1$H NMR (CDCl$_3$) δ 8.0-7.4 (m, 20, fluorenyl-H), 7.3 and 6.8 (AB doublet, 8,9-arylH), 4.1 (t, 4, arOCH$_2$), 3.7 (t, 8, morpholine OCH$_2$), 2.75 (t, 4, arOCH$_2$C$\underline{H}_2$N), 2.5 (t, 8, morpholine-NCH$_2$), 2.08 (t, 8, 9-CH$_2$R), 1.3-1.0 (m, 40, 9-CH$_2$(C$\underline{H}_2$)$_5$CH$_2$CH$_3$), 0.8 (t, 12, 9-CH$_2$(CH$_2$)$_5$CH$_2$C$\underline{H}_3$) and 0.7 ppm (m, 8,9-CH$_2$(CH$_2$)$_5$C$\underline{H}_2$CH$_3$)

Example 8B

Preparation of 9,9-dioctyl-2-(9,9-bis-4-(2-morpholinoethoxyphenyl)-2,5-bis-9,9-dioctylfluoren-2-yl

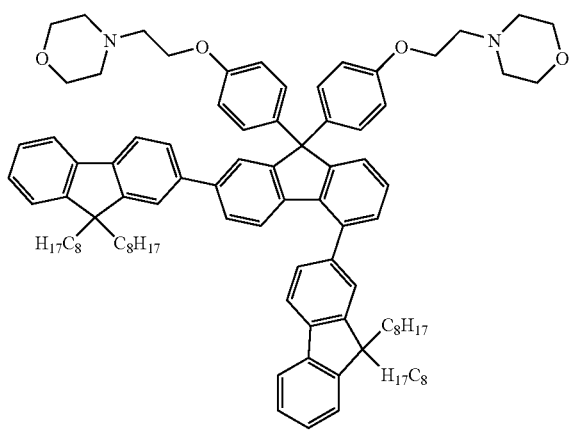

Materials: 9,9-bis-4-(2-morpholinoethoxy)phenyl-2,5-dibromofluorene is prepared by alkylation of 9,9-bis-4-hydroxyphenyl-2,5-dibromofluorene with 2-chloroethyl morpholine hydrochloride with 50% NaOH/toluene in the presence of Adogen 464 as a phase transfer catalyst; 9,9-dioctyl-2-neopentylglycol boronate is prepared by lithiation of 9,9-dioctylfluorene (BuLi, Et$_2$O/−78° C.) followed by borylation (triethoxy borate), hydrolysis and re-esterification with neopenyl glycol.

Preparation of trimer: A solution of 9,9-bis-4-(2-morpholinoethoxy)phenyl-2,5-dibromofluorene, 1.101 g (1.5 mmol), 9,9-dioctyl-2-neopentylglycol boronate, 1.544 g (3.075 mmol) and dicyclohexyl-2-(2,6-dimethoxyphenyl)phenylphosphine, 0.054 g (0.131 mmol) in toluene (30 ml) is degassed for 15 minutes then Pd(OAc)$_2$, 0.084 g (0.0375 mmol) and 10% aqueous tetraethylammonium hydroxide, 11 g that had been separately degassed is added. The stirred mixture is immersed in a 70° C. oil bath and stirred under nitrogen for 18 hrs. The cooled mixture is filtered and transferred to a separatory funnel. The aqueous phase is discarded and the organic phase is washed with water (3×50 ml) and brine (1×50 ml) then passed through a cone of anhydrous CaSO$_4$. Removal of solvent affords a white foam that is purified by chromatography on 80 g of alumina (neutral).

Device Fabrication

The following examples describe the fabrication and evaluation of devices made using either polymer 2 or a commercially available poly-2,7-fluorene (ADS-131) as the emissive layers. Test OLED devices fabricated using polymer 2 as the light-emitting layer performed comparably to similar devices made using a commercially available poly-2,7-fluorene (ADS-131) as the light-emitting layer.

Example 9

OLED with 2,5-Fluorene Polymer

A layer of PEDOT/PSS (Baytron P VP 8000, a poly(3,4-ethylenedioxythiophene)-poly(styrenesulfonate) obtained as a solution from HC Starck, Inc.) having a thickness of about 60 nm was deposited by spin-coating onto clean, UV-Ozone treated, 2.5 cm×2.5 cm ITO patterned glass substrates. The coated substrates were then baked on a hot plate in air for 30 minutes at 160° C. A layer of electroluminescent polymer 2 was deposited from solution atop the F8-TFB layer. This layer had a thickness of approximately 40-50 nm as measured by profilometry.

A bilayer (NaF, Al) cathode was deposited. The coated substrates were then placed into a bell jar evaporator, and the system was pumped until a pressure of about 1×10$^{-6}$ torr was obtained. A layer of sodium fluoride about 3 nm thick (as measured via a calibrated quartz crystal microbalance) was then deposited atop the final layer of the coated substrates by physical vapor deposition. Subsequently, a layer of aluminum metal about 130 nm thick was deposited atop the sodium fluoride layer by vapor deposition under vacuum to form the cathode component of the OLED Example 10

OLED with 2,5-Fluorene Polymer and TFB Interlayer

A layer of PEDOT/PSS (Baytron P VP 8000, a poly(3,4-ethylenedioxy-thiophene)-poly(styrenesulfonate) obtained as a solution from HC Starck, Inc.) having a thickness of about 60 nm was deposited by spin-coating onto clean, UV-Ozone treated, 2.5 cm×2.5 cm ITO patterned glass substrates. The coated substrates were then baked on a hot plate in air for 30 minutes at 160° C. A layer of F8-TFB (an octylfluorene-triarylamine copolymer obtained from Sumation, Inc.) hole transporter layer having a thickness of about 10-20 nm was then spin-coated atop the PEDOT/PSS coated substrates. The F8-TFB-PEDOT/PSS coated substrates were then baked on a hot plate in argon for 30 minutes at 170° C. A final layer of electroluminescent polymer 2 was deposited from solution atop the F8-TFB layer. This layer had a thickness of approximately 40-50 nm.

A bilayer (NaF, Al) cathode was deposited. The coated substrates were then placed into a bell jar evaporator, and the system was pumped until a pressure of about 1×10⁻⁶ torr was obtained. A layer of sodium fluoride about 3 nm thick (as measured via a calibrated quartz crystal microbalance) was then deposited atop the final layer of the coated substrates by physical vapor deposition. Subsequently, a layer of aluminum metal about 130 nm thick was deposited atop the sodium fluoride layer by vapor deposition under vacuum to form the cathode component of the OLED.

Example 11

OLED with 2,5-Fluorene Polymer/TFB Blend, TFB interlayer

A layer of PEDOT/PSS (Baytron P VP 8000, a poly(3,4-ethylenedioxy-thiophene)-poly(styrenesulfonate) obtained as a solution from HC Starck, Inc.) having a thickness of about 60 nm was deposited by spin-coating onto clean, UV-Ozone treated, 2.5 cm×2.5 cm ITO patterned glass substrates. The coated substrates were then baked on a hot plate in air for 30 minutes at 160° C. A layer of F8-TFB (an octylfluorene-triarylamine copolymer obtained from Sumation, Inc.) hole transporter layer having a thickness of about 10-20 nm was then spin-coated atop the PEDOT/PSS coated substrates. The F8-TFB-PEDOT/PSS coated substrates were then baked on a hot plate in argon for 30 minutes at 170° C. A final layer of the consisting of a blend of electroluminescent polymer (JC392-147) with F8-TFB (90:10 ratio) was deposited from solution atop the F8-TFB layer. This layer had a thickness of approximately 40-50 nm.

A bilayer (NaF, Al) cathode was deposited. The coated substrates were then placed into a bell jar evaporator, and the system was pumped until a pressure of about 1×10⁻⁶ torr was obtained. A layer of sodium fluoride about 3 nm thick (as measured via a calibrated quartz crystal microbalance) was then deposited atop the final layer of the coated substrates by physical vapor deposition. Subsequently, a layer of aluminum metal about 130 nm thick was deposited atop the sodium fluoride layer by vapor deposition under vacuum to form the cathode component of the OLED Comparative Example OLED with 2,7-Fluorene and TFB Interlayer A layer of PEDOT/PSS (Baytron P VP 8000, a poly(3,4-ethylenedioxythiophene)-poly(styrenesulfonate) obtained as a solution from HC Starck, Inc.) having a thickness of about 60 nm was deposited by spin-coating onto clean, UV-Ozone treated, 2.5 cm×2.5 cm ITO patterned glass substrates. The coated substrates were then baked on a hot plate in air for 30 minutes at 160° C. A layer of F8-TFB (an octylfluorene-triarylamine copolymer obtained from Sumation, Inc.) hole transporter layer having a thickness of about 10-20 nm was then spin-coated atop the PEDOT/PSS coated substrates. The F8-TFB-PEDOT/PSS coated substrates were then baked on a hot plate in argon for 30 minutes at 170° C. A final layer of the electroluminescent polymer ADS131 (a polyfluorene obtained from American Dye Source) obtained was deposited from solution atop the F8-TFB layer. This layer had a thickness of approximately 40-50 nm.

A bilayer (NaF, Al) cathode was deposited. The coated substrates were then placed into a bell jar evaporator, and the system was pumped until a pressure of about 1×10⁻⁶ torr was obtained. A layer of sodium fluoride about 3 nm thick (as measured via a calibrated quartz crystal microbalance) was then deposited atop the final layer of the coated substrates by physical vapor deposition. Subsequently, a layer of aluminum metal about 130 nm thick was deposited atop the sodium fluoride layer by vapor deposition under vacuum to form the cathode component of the OLED.

The Lumen per Watt (LPW), external quantum efficiency (EQE) and Current versus voltage (IV) and spectral characteristics were measured for each of the OLEDs described in the examples. To measure the IV characteristics of each device, a voltage was applied and the resulting current response determined using a Keithley 237 Source measure unit. The luminous output in terms of candela/meter² was simultaneously measured using a silicon diode calibrated against a Minolta LS 100 luminance meter. To convert from cd/m² as measured on the luminance meter to lumens, a Lambertian emission pattern was assumed and the following equation was used. Lumens=(cd/m²)×(device area)×(π). The spectrum of each OLED described in the example was measured using a CCD camera mounted on a ¼ meter Acton research spectrometer. The relative spectral response of the CCD/spectrometer combination was calibrated using a calibrated incandescent lamp. The spectra measurements determine the CIEx and CIEy points as well as permit conversion of the LPW data into EQE data. A summary of the device performance datameasured at a current density of 10 ma/cm² is shown in Table 3. The device data below indicates that these OLED devices made from the materials described in this invention exhibit comparable EQE performance to the control 2-7 poly-fluorene materials. This suggests their broad suitability as fundamental building blocks for a variety of electroluminescent materials.

TABLE 3

|  | Layer Structure | V | cd/m^2 | %EQE | CIEx | CIEy |
|---|---|---|---|---|---|---|
| Comparative Example | PEDOT/TFB/ADS131 | 4.690246 | 1.322123 | 1.1 | 0.180 | 0.140 |
| Example 9 | PEDOT/Polymer 2 | 4.216768 | 0.413992 | 0.8 | 0.163 | 0.099 |
| Example 10 | PEDOT/TFB/Polymer2 | 5.148998 | 0.438272 | 1.4 | 0.157 | 0.058 |
| Example 11 | PEDOT/TFB/10%TFB, 90% Polymer 2 | 5.095477 | 0.819261 | 0.55 | 0.154 | 0.061 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A compound of formula I

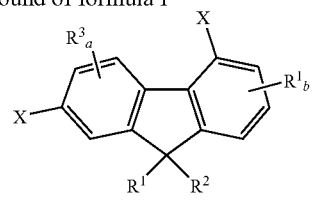

I

23 wherein R¹ and R² are independently at each occurrence C₁₋₂₀ hydrocarbyl, C₁₋₂₀ hydrocarbyl containing one or more S, N, O, P or Si atoms, C₄₋₁₆ hydrocarbyl carbonyloxy, C₄₋₁₆ aryl(trialkylsiloxy) or R¹ and R² taken together with an intervening carbon atom form a C₅₋₂₀ hydrocarbyl ring or a C₄₋₂₀ hydrocarbyl ring containing at least one S, N or O heteroatom;

R³ and R⁴ are independently at each occurrence C₁₋₂₀ hydrocarbyl, C₁₋₂₀ hydrocarbyloxy, C₁₋₂₀ thioether, C₁₋₂₀ hydrocarbylcarbonyloxy or cyano;

X is independently at each occurrence halo, triflate, —B(OH)₂, —B(OR)₂, —BO₂R, or a combination thereof;

R is alkyl or alkylene; and a and b are independently 0 or 1.

2. A compound according to claim 1, wherein X is halo.

3. A compound according to claim 1, wherein X is bromo.

4. A compound according to claim 1, wherein X is —B(OH)₂, —B(OR)₂, or —BO₂R.

5. A compound according to claim 1, wherein R³ and R⁴ are H.

6. A compound according to claim 1, wherein R¹ and R² are alkyl, substituted alkyl, aryl, substituted aryl, heteroaryl, or substituted heteroaryl.

7. A compound according to claim 1, wherein R¹ and R² are alkoxyphenyl.

8. A compound according to claim 1, wherein R¹ and R² are alkyl.

9. A compound according to claim 1, of formula

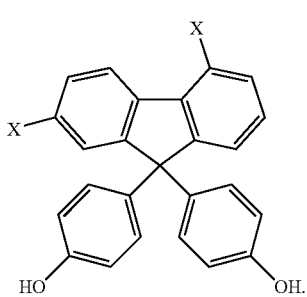

10. A compound according to claim 1, of formula

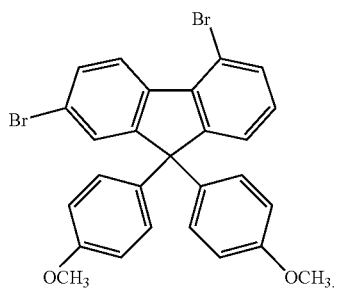

24

11. A compound according to claim 1, of formula

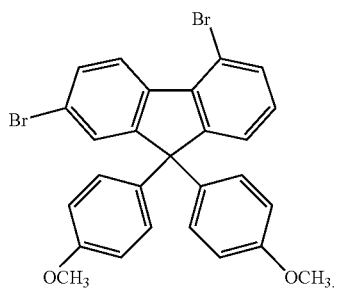

12. A compound according to claim 1, of formula

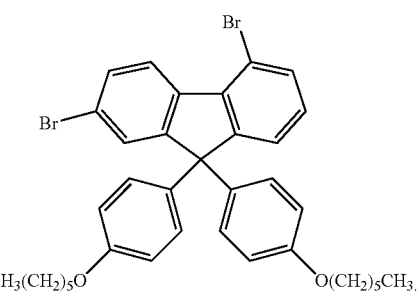

13. A compound according to claim 1, of formula

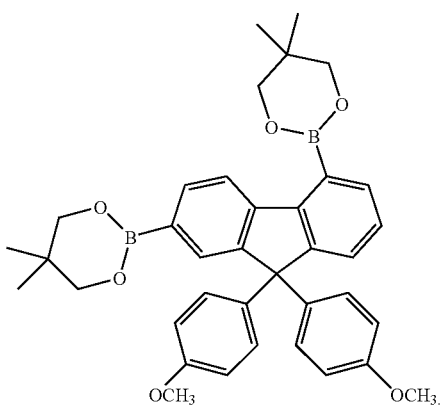

14. A compound of formula II wherein R¹ and R² are independently at each occurrence H, C₁₋₂₀ hydrocarbyl, C₁₋₂₀ hydrocarbyl containing one ormore S, N, O, P or Si atoms, $C_{4-16}$ hydrocarbyl carbonyloxy, $C_{4-16}$ aryl(trialkylsiloxy) or $R^1$ and $R^2$ taken together with an intervening carbon atom form a $C_{5-20}$ hydrocarbyl ring or a $C_{4-20}$ hydrocarbyl ring containing at least one S, N or O heteroatom;

$R^3$ and $R^4$ are independently at each occurrence H, $C_{1-20}$ hydrocarbyl, $C_{1-20}$ hydrocarbyloxy, $C_{1-20}$ thioether, $C_{1-20}$ hydrocarbylcarbonyloxy or cyano;

one of X and Y is halo or triflate and the other one of X and Y is $-B(OH)_2$, $-B(OR)_2$, or $-BO_2R$;

R is alkyl or alkylene; and a and b are independently 0 or 1.

15. A compound according to claim 14, wherein X is halo and Y is $-B(OH)_2$, $-B(OR)_2$, or $-BO_2R$.

16. A compound according to claim 14, wherein X is $-B(OH)_2$, $-B(OR)_2$, or $-BO_2R$ and Y is halo.

17. A compound according to claim 14, wherein one of X and Y is bromo and the other one of X and Y is $-BO_2R$.

18. A compound according to claim 14, wherein $R^3$ and $R^4$ are H.

19. A compound according to claim 14, wherein $R^1$ and $R^2$ are alkyl, substituted alkyl, aryl, substituted aryl, heteroaryl, or substituted heteroaryl.

20. A compound according to claim 14, wherein $R^1$ and $R^2$ are alkoxyphenyl.

21. A compound according to claim 14, wherein $R^1$ and $R^2$ are alkyl.

22. A compound according to claim 14, of formula

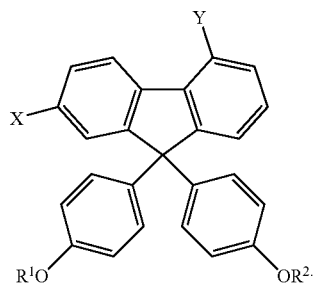

23. A compound according to claim 14, of formula

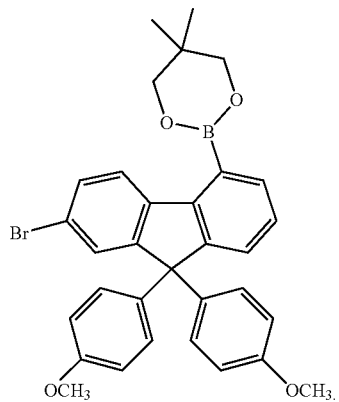

* * * * *

UNITED STATES PATENT AND TRADEMARK OFFICE
CERTIFICATE OF CORRECTION

| | | |
|---|---|---|
| PATENT NO. | : 7,635,792 B1 | Page 1 of 1 |
| APPLICATION NO. | : 12/250807 | |
| DATED | : December 22, 2009 | |
| INVENTOR(S) | : Cella et al. | |

It is certified that error appears in the above-identified patent and that said Letters Patent is hereby corrected as shown below:

On the Title Page, in Field (75), under "Inventors", in Column 1, Line 5, delete "Smigelski," and insert -- Smigelski, Jr., --, therefor.

In Column 5, Line 57, delete "II," and insert -- III, --, therefor.

In Column 13, Line 10, delete "(4-hexyl-oxy)" and insert -- (4-hexyloxy) --, therefor.

In Column 14, Line 14, delete "$OC_3H_{13}$" and insert -- $OC_6H_{13}$ --, therefor.

In Column 16, Structure 4, delete "and".

In Column 22, Line 61, Structure I, delete "$R^1_b$" and insert -- $R^4_b$ --, therefor.

Signed and Sealed this

Ninth Day of February, 2010

David J. Kappos
*Director of the United States Patent and Trademark Office*